(12) United States Patent
Damarati

(10) Patent No.: US 7,150,750 B2
(45) Date of Patent: Dec. 19, 2006

(54) METHOD AND DEVICE FOR ENDOSCOPIC SUTURING

(75) Inventor: John Jairo Damarati, Tokyo (JP)

(73) Assignee: Boston Scientific Scimed, Inc., Maple Grove, MN (US)

(*) Notice: Subject to any disclaimer, the term of this patent is extended or adjusted under 35 U.S.C. 154(b) by 28 days.

(21) Appl. No.: 10/045,975

(22) Filed: Jan. 10, 2002

(65) Prior Publication Data

US 2003/0130669 A1 Jul. 10, 2003

(51) Int. Cl.
*A61B 17/56* (2006.01)
(52) U.S. Cl. .................. 606/72; 606/139; 606/144
(58) Field of Classification Search .............. 606/72, 606/232, 139, 144, 148, 142, 143, 75, 104
See application file for complete search history.

(56) References Cited

U.S. PATENT DOCUMENTS

| 5,207,679 | A | * | 5/1993 | Li ............................ 606/72 |
| 5,242,456 | A | * | 9/1993 | Nash et al. ............... 606/142 |
| 5,437,680 | A | * | 8/1995 | Yoon ........................ 606/139 |
| 5,549,631 | A | | 8/1996 | Bonutti |
| 5,662,654 | A | * | 9/1997 | Thompson ................ 606/72 |
| 5,810,848 | A | | 9/1998 | Hayhurst |
| 5,891,168 | A | | 4/1999 | Thal |
| 6,447,524 | B1 | * | 9/2002 | Knodel et al. ........... 606/151 |
| 2002/0022851 | A1 | * | 2/2002 | Kalloo et al. ........... 606/151 |
| 2002/0156500 | A1 | * | 10/2002 | Storz-Irion et al. ..... 606/232 |

FOREIGN PATENT DOCUMENTS

| EP | 0 641 546 A1 | 3/1995 |
| WO | WO 01/80746 A1 | 11/2001 |
| WO | WO 02/053011 A2 | 7/2002 |

\* cited by examiner

*Primary Examiner*—Anhtuan T. Nguyen
*Assistant Examiner*—Darwin P Erezo
(74) *Attorney, Agent, or Firm*—Fay Kaplun & Marcin, LLP

(57) ABSTRACT

A device for suturing an opening in an internal organ of a patient, comprises a first catheter for insertion to an opening to be sealed through a working channel of an endoscope, a plurality of anchoring members received within the first catheter, each of the anchoring members including a shaft extending from a tissue penetrating distal tip to a suture receiving proximal end and a gripping arm moveable between an insertion configuration in which the gripping arm is folded against the shaft and a gripping configuration in which the gripping member extends away from the shaft and a driving member extending through the first catheter to a proximal end thereof, wherein advancing the driving member distally into the first catheter advances the anchoring members distally through the first catheter to drive a distal-most one of the anchoring members out of the first catheter to anchor in tissue. A length of suture extends between the suture receiving proximal ends of the anchor members.

11 Claims, 10 Drawing Sheets

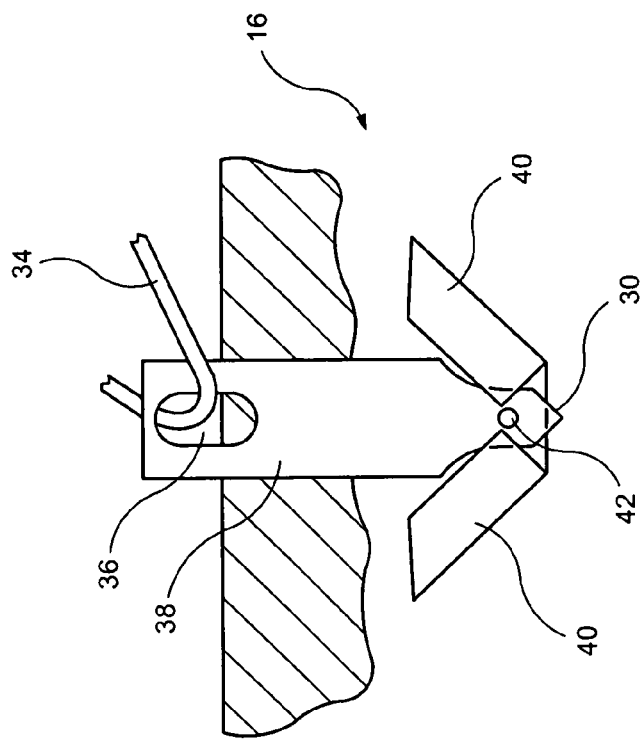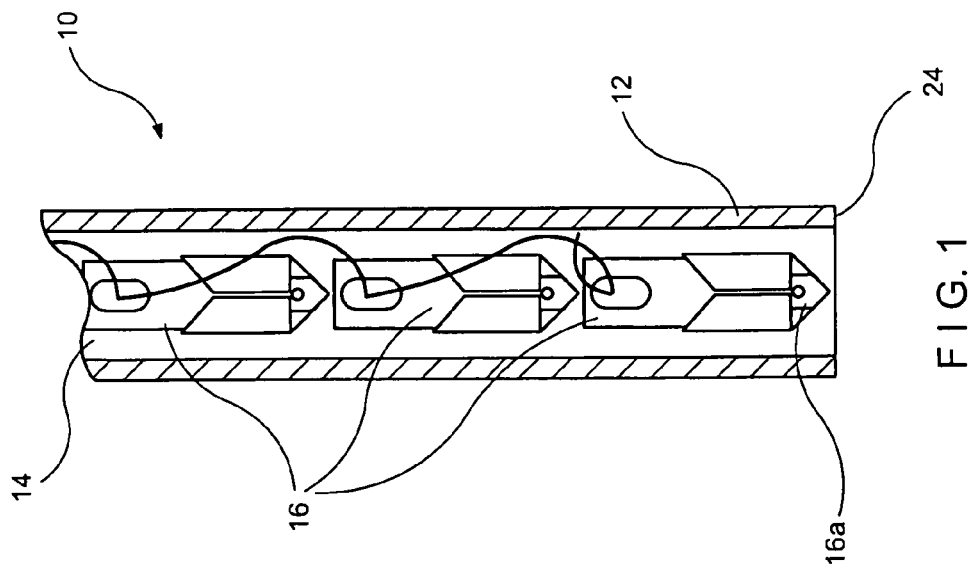

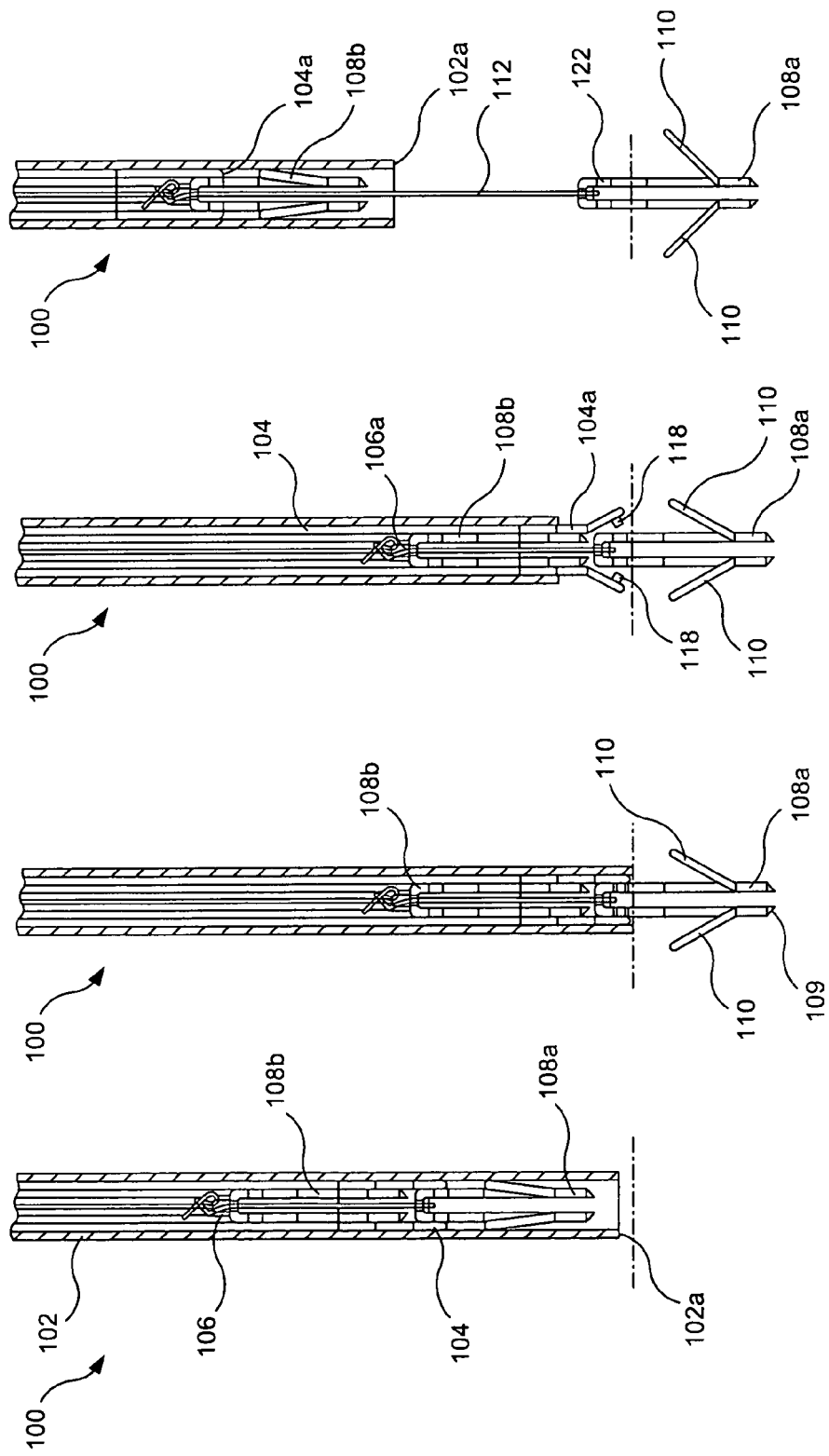

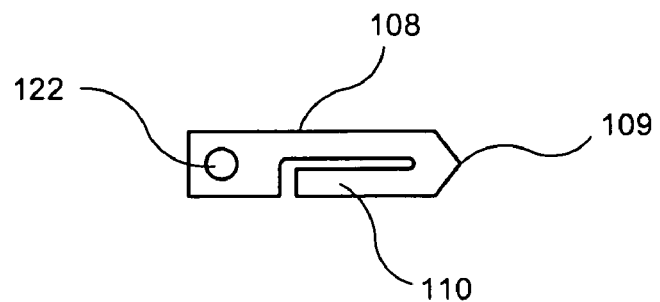
F I G. 12
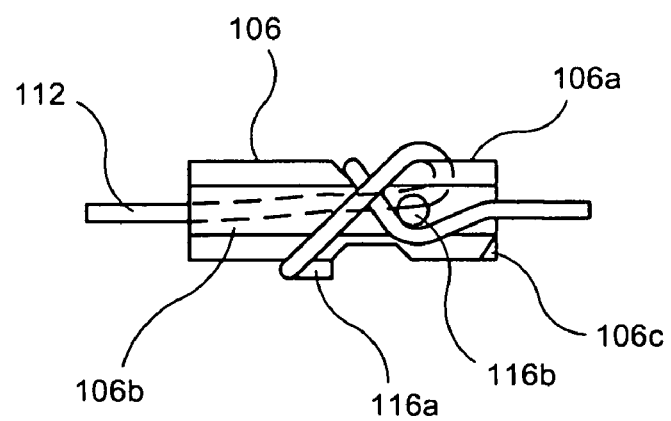
F I G. 13

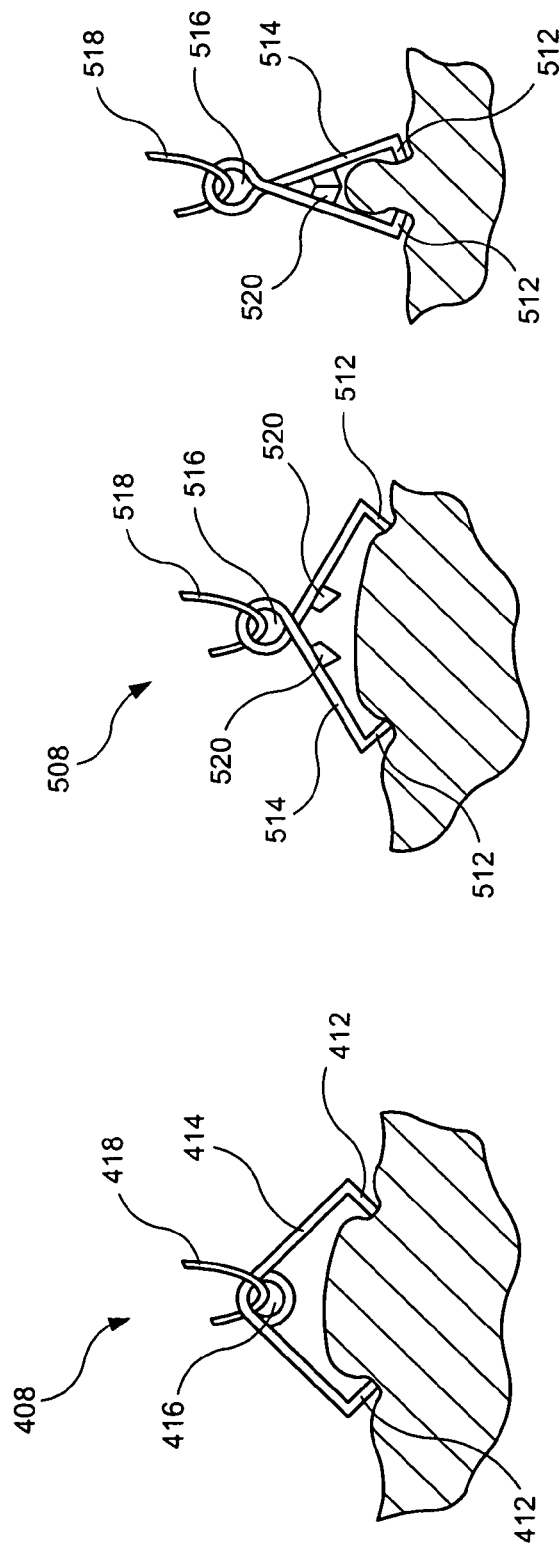

METHOD AND DEVICE FOR ENDOSCOPIC SUTURING

BACKGROUND INFORMATION

The present invention relates to methods and devices for achieving hemostasis and more particularly relates to endoscopic methods and devices for achieving hemostasis.

Currently, hemostasis is addressed endoscopically by injection therapy, contact thermal or electrocoagulation or mechanical hemoclips. However, each of these techniques has drawbacks. For example, the agents injected in injection therapy may enter the blood stream and produce undesired side effects and each of these methods may, under certain conditions, fail to achieve the desired hemostasis. When any of these methods fails to adequately stop the bleeding, emergency surgery is performed and a surgeon sutures the bleeding wound closed.

These methods have been employed, for example, in the treatment of bleeding which arises naturally as in the case of Peptic Ulcer Disease (PUD) as well as bleeding resulting from surgical procedures such as endoscopic mucosal resection (EMR). However, such post EMR lesions may be too large to achieve the required hemostasic and/or to promote healing of the surrounding tissue.

SUMMARY OF THE INVENTION

The present invention is directed to a device for suturing an opening in an internal organ of a patient, comprising a first catheter for insertion to an opening to be sealed through a working channel of an endoscope, a plurality of anchoring members received within the first catheter, each of the anchoring members including a shaft extending from a tissue penetrating distal tip to a suture receiving proximal end and a gripping arm moveable between an insertion configuration in which the gripping arm is folded against the shaft and a gripping configuration in which the gripping member extends away from the shaft and a driving member extending through the first catheter to a proximal end thereof, wherein advancing the driving member distally into the first catheter advances the anchoring members distally through the first catheter to drive a distal-most one of the anchoring members out of the first catheter to anchor in tissue. A length of suture extends between the suture receiving proximal ends of the anchor members.

BRIEF DESCRIPTION OF THE DRAWINGS

FIG. 1 shows a cross-sectional view of a device according to a first embodiment of the present invention;

FIG. 2 shows a perspective view of an anchoring member of the device of FIG. 1 anchored within tissue to be sutured;

FIG. 7 shows a cross-sectional view of a device according to a second embodiment of the invention in four positions;

FIG. 12 shows a side view of an anchoring clip of the device of FIG. 7;

FIG. 13 shows a cross-sectional view of a distal end of an inner catheter of the device of FIG. 7;

FIG. 16 shows a side view of an anchoring clip according to a third alternate embodiment of the invention; and FIG. 17 shows a side view of an anchoring clip according to a fourth alternate embodiment of the invention in initial and fully deployed positions.

DETAILED DESCRIPTION

Figure 5:
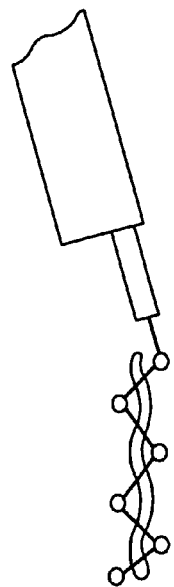
FIG. 5 shows the perspective view of FIG. 4a with the suture drawn tight to close the opening to be sealed.
Figure 6:
FIG. 6 shows the perspective view of FIG. 4a with the suture drawn tight to close the opening to be sealed with the device of FIG. 1 removed and the suture severed and fixed in place.

The present invention may be further understood with reference to the following description and the appended drawings, wherein like elements are provided with the same reference numerals. The present invention provides an endoscopic method and device for endoscopic suturing to achieve hemostasis.

Figure 3:
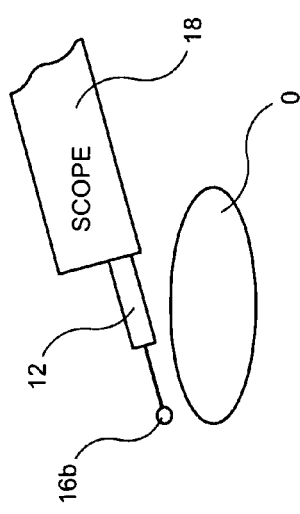
FIG. 3 shows a perspective view of the device of FIG. 1 adjacent to an opening to be sealed.
Figure 4:
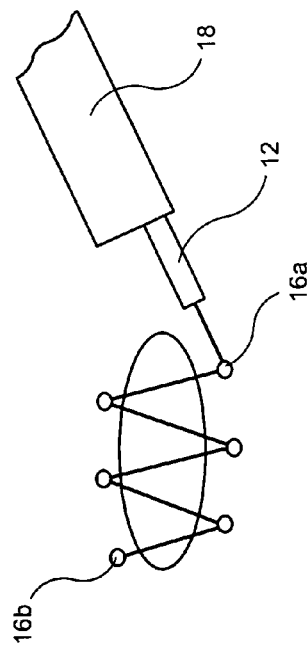
FIG. 4 shows a perspective view of the device of FIG. 1 adjacent to an opening to be sealed with sutures extending between anchoring members anchored within the tissue to be sutured.

In particular, as shown in FIGS. 1–6, an apparatus 10 according to a first embodiment of the present invention comprises a flexible tube 12 including a central lumen 14 within which a plurality of anchoring members 16 are received. Those skilled in the art will understand that the tube 12 may, for example, be composed of a coil of bio-compatible metal such as, for example, stainless steel or an extruded polymer. The tube 12 is axially stiff to withstand forces of tension and compression exerted thereon during use, but is flexible to permit bending of the tube 12 during insertion through an endoscope 18. The tube 12 extends between a handle (not shown) coupled to a proximal end thereof and a distal end 24. As shown in FIGS. 3 and 4, the tube 12 is sized so that it may be passed through a working channel of the endoscope 18. For example, an outer diameter of the tube 12 may preferably be between 6 and 9 french. Of course, those of skill in the art will understand that the tube 12 may alternatively be formed with a larger outer diameter and may be made of a rigid material for applications with, for example, a rigid laparascope or for open surgery. The anchoring members 16 abut one another within the lumen 14 and a pushing piston (not shown) abutting a proximal end of a proximal-most one of the anchoring members 16a extends through the lumen 14 to couple to an actuator on the handle. Thus, actuation of the actuator 28 moves the pushing piston distally into the lumen 14 moving the proximal-most anchoring member 16a and all anchoring members 16 received distally thereof toward the distal end 24.

Each of the anchoring members 16 according to the first embodiment of the invention includes a pointed, tissue penetrating, distal tip 30 which, when received within the lumen 14, faces a distal opening 32 thereof. A length of suture 34 extends between the anchoring members 16 passing through an eyelet 36 formed at a proximal end of a shaft 38 of each of the corresponding anchoring members 16. A distal end of the suture 34 is coupled to the eyelet 36 of the distal-most one of the anchoring members 16b and extends therefrom sequentially through each of the eyelets 36 of the remaining anchoring members 16 in order, distal to proximal. The length of suture 34 extends through the eyelet 36 of the proximal-most one of the anchoring members 16a, through the lumen 14 and out of the proximal end of the tube 12 so that a second end of the length of suture 34 is accessible to a user. As would be understood by those of skill in the art, the suture 34 may be formed of any bio-degradable, bio-absorbable or bio-compatible material such as polyglycolic acid, polyactic acid, etc. Furthermore, those of skill in the art will understand that, alternatively, the length of suture 34 may extend through all of the eyelets 36 including that of the distal-most one of the anchoring members 16b so that a look of the suture 34 extends from the first end outside the body and accessible to the user, through the lumen 14, through each of the eyelets 36 and back through the lumen 14 to the second end which is also accessible to the user.

As shown in FIG. 2, each of the anchoring members 16 includes a pair of retractable arms 40 pivotally coupled to the shaft 38 by a pin 42 so that the arms 40 may rotate between a retracted position as shown in FIG. 1 and an extended position shown in FIG. 2. In the retracted position, the arms 40 are folded along the shaft so that the diameter of the anchoring member 16 is less than an inner diameter of the lumen 14. While within the lumen 14, the arms 40 are maintained in the retracted position by the inner wall of the lumen 14.

Figure 11A:
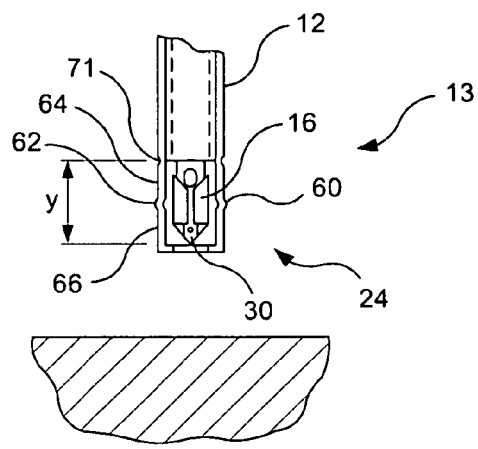
FIG. 11a shows a cross-sectional view of the device of FIG. 1 including a contact pressure mechanism according to an exemplary embodiment of the invention prior to contacting tissue.
Figure 11B:
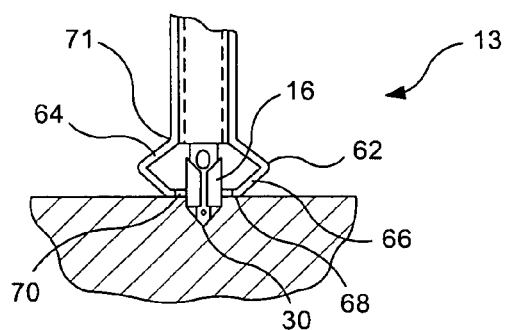
FIG. 11b shows a cross-sectional view of the device of FIG. 11a in contact with the tissue with a tissue penetrating tip of an anchoring member within the tissue.
Figure 11C:
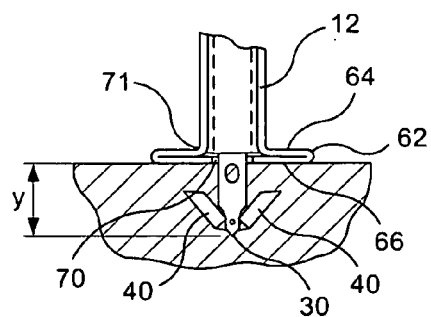
FIG. 11c shows a cross-sectional view of the device of FIG. 11a with the contact pressure mechanism fully deployed against the tissue.

When the anchoring member 16 has been removed from the lumen 14, the arms 40 are deployed to the extended under control of a contact pressure mechanism 13 shown in more detail in FIGS. 11a–11c. The contact pressure mechanism 13 ensures that the arms 40 are deployed only when the pointed distal tip 30 of the anchoring member 16 is in contact with the tissue and prevents the tube 12 from penetrating the tissue and ensures that the anchoring member 16 is deployed to a desired depth to sufficiently anchor itself within the tissue. Specifically, the contact pressure mechanism 13 formed at the distal end 24 of the tube 12 includes a bellows-section 60 with a first hinge 62 connecting the distal ends of a set of proximal arms 64 to the proximal ends of a corresponding set of distal arms 66. A second hinge 68 connects distal ends of at least a portion of the distal arms 66 to corresponding anchoring member gripping arms 70. A third hinge 71 connects the proximal ends of the proximal arms 66 to the body of the tube 12.

As seen in FIG. 11a, the contact pressure mechanism 13 is biased so that, when in an initial position out of contact with the tissue, the proximal arms 64, the distal arms 66 and the gripping arms 68 are maintained substantially parallel with an outer surface of the tube 12. As shown in FIG. 11b, when the tube 12 is distally advanced so that the distal end 24 contacts the tissue, the gripping arms 68 are rotated inward so that an outer surface of each gripping arm 68 lays on the surface of the tissue pointing radially inward within the tube 12 with the ends of the gripping arms abutting against the retractable arms 40 to maintain the retractable arms 40 in the retracted position. At this point, the proximal arms 64 and the distal arms 66 are rotated about the first hinge 62 so that the first hinge 62 is moved radially outward from the tube 12 until, as shown in FIG. 11c, outer surfaces of the distal arms 66 lay against the surface of the tissue.

Furthermore, as the contact pressure mechanism 13 is radially expanded and axially compressed from the initial configuration of FIG. 11a to the final configuration of FIG. 11c, the distal opening of the tube 12 moves proximally to expose the distal tip 30 of the distal-most anchoring member 16 so that the tip 30 penetrates the tissue. As the tip 30 is pushed further into the tissue, the gripping arms 68 hold the retractable arms 40 in the retracted position until proximal ends of the retractable arms 40 have moved distally past the gripping arms 68. By this point, a portion of the retractable arms 40 will be received within the tissue and the tissue will hold the arms in the retracted position until the user deploys the arms (e.g., by pulling the anchoring member 16 proximally so that contact between the proximal ends of the retractable arms 40 and the tissue draws the arms radially outward into the deployed configuration). As will be understood by those of skill in the art, a length Y of the bellows section 60 when in the unbiased, fully extended configuration, is approximately equal to the depth Y within the tissue of the distal tip 30 when the arms 40 are released by the gripping arms 70.

Those skilled in the art will understand that the anchoring members 16 may be formed of any bio-absorbable, biodegradable or bio-compatible material including, for example, alloy metals, compound plastics, ceramics, etc. as would be understood by those of skill in the art. For example, the anchoring members 16 may be formed of titanium.

In operation, the endoscope 18 is positioned adjacent to an opening O in an organ to be sealed such as, for example, an opening created by an endoscopic mucosal resection procedure or a PUD lesion and the tube 12 is inserted into a working channel of the endoscope 18 and advanced to the distal end of the endoscope 18 as would be understood by those of skill in the art. The tube 12 is then advanced out of the distal end of the endoscope 18 to a desired position for the distal-most anchoring member 16b adjacent to the opening O. The desired position of placement for the first anchoring member 16 is preferably selected adjacent to a distal-most end of the opening O. The user then operates the actuator 28 to move the pushing piston 26 distally into the lumen 14, driving the distal-most anchoring member 16b out of the distal end 24 of the tube 12 and into the tissue at the desired location. Once the tip 30 of the distal-most anchoring member 16b has penetrated the tissue to a desired depth, the contact pressure mechanism 13 operates to deploy the arms 40 to lock the anchoring member 16b in position in the tissue at the desired location. The user then repositions the distal end 24 of the tube 12 adjacent to a desired position for a second one of the anchoring members 16. The user preferably selects the positions into which the anchoring members 16 will be placed on alternate sides of the opening O similarly to the positions through which a user would pass a needle in conventional suturing. As shown in FIG. 4, the suture 34 extends through the eyelet 36 of the anchoring member 16b to the eyelet 36 of the second one of the anchoring members 16. The user then repeats this procedure, placing each of the anchoring members 16 in the desired positions until the proximal-most anchoring member 16a has been successfully deployed. As shown in FIG. 5, the user then draws the suture 34, the distal end of which is coupled to the eyelet 36 of the distal-most anchoring member 16b, proximally from the tube 12, drawing the anchoring members 16 and the tissue within which they are embedded together and closing the opening O.

A system 100 according to a second embodiment of the invention is shown in FIGS. 7–12. The system 100 includes 3 nested catheters 102, 104 and 106 with the catheter 106 being slidably received within the catheter 104 and the catheter 104 slidably received within the catheter 102. Similarly to the tube 12, the catheter 102 may, for example, be composed of a coil of bio-compatible metal such as stainless steel or an extruded polymer. The catheter 102 is flexible to permit bending thereof during insertion through a working channel of an endoscope and extends between a handle coupled to a proximal end thereof and a distal end 102a. Anchoring clips 108 are received within the catheter 104 with distal, tissue penetrating points 109 of the anchoring clips 108 facing distal ends 104a and 102a of the catheters 104 and 102, respectively. While within the catheter 104, the inner surface of the lumen 104b of the catheter 104 maintains projecting members 110 in a retracted configuration folded back along the respective anchoring clip 108 as shown for the proximal-most anchoring clip 108b in FIG. 7, positions 1) and 2). These projecting members 110 are biased radially outward from the body of the anchoring clips 108 so that, when one of the anchoring clips 108 is advanced distally beyond the distal end 104a of the catheter 104, the projecting members 110 spring outward until they contact the inner surface of the catheter 102, as shown for the distal-most anchoring clip 108a in position 1 in FIG. 7 and the proximal-most anchoring member 108b in position 4).

Then, when the anchoring clip 108 is advanced further distally beyond the distal end 102a of the catheter 102, the projecting members 110 deploy fully to the extended position as shown in FIG. 7 positions 2)–4). A length of suture 112 is coupled to the proximal end of the distal-most anchoring clip 108a and extends from there to the proximal ends of each succeeding anchoring clip 108 until it passes through the proximal end of the proximal-most anchoring clip 108b. Those skilled in the art will understand that, although the figures show only 2 anchoring clips 108 for this embodiment, that any number of anchoring clips 108 may be included between the distal-most and proximal-most anchoring clips 108a, 108b, respectively.

Figure 9:
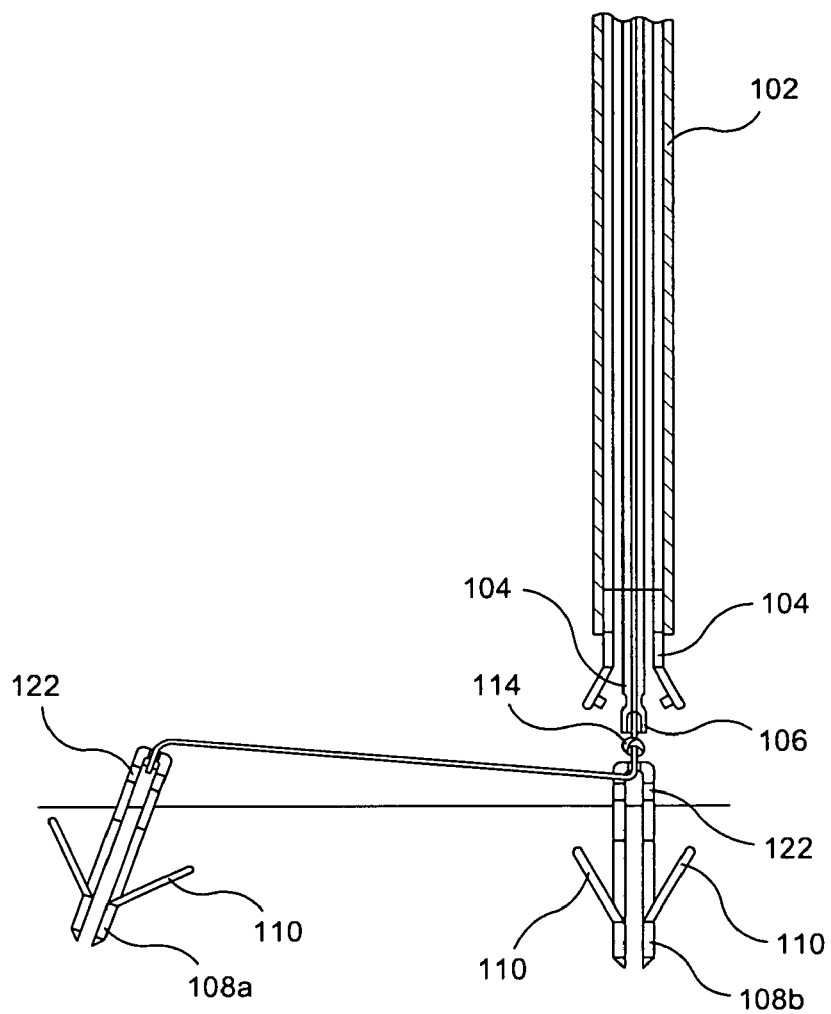
FIG. 9 shows a cross-sectional view of the device of FIG. 7 with first and second anchoring members embedded in tissue and the length of suture extending therebetween tightened with a knot.
Figure 10:
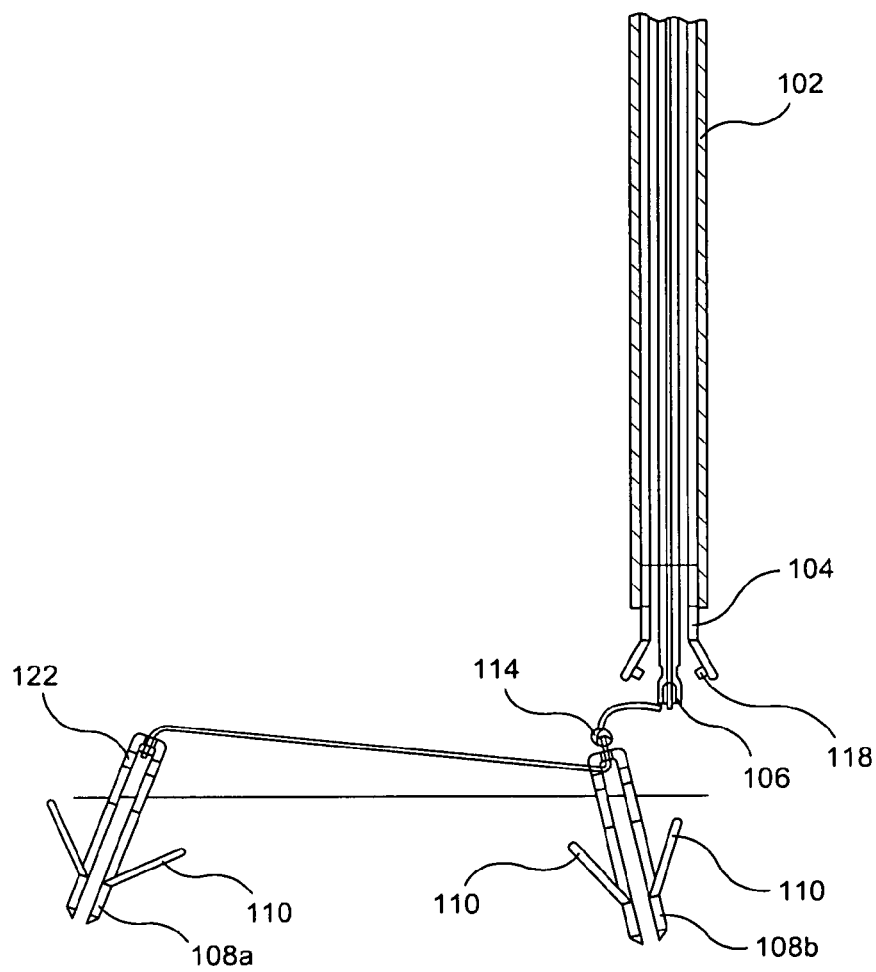
FIG. 10 shows a cross-sectional view of the device of FIG. 7 with first and second anchoring members embedded in tissue and the length of suture severed from the device.

As shown in FIGS. 9, 10 and 13, the suture 112 passes from the proximal-most anchoring clip 108b to wrap around a distal end 106a of the catheter 106 and extend through a lumen 106b formed therein to the proximal end of the endoscope where the suture 112 is accessible to the user. Also formed at the distal end 106a of the catheter 106 is a suture cutting surface 106c. Prior to insertion of the catheters 102, 104, 106 into the endoscope, a knot 114 is formed around the end of the catheter 106 and held in place thereon by pins 116a and 116b as shown in FIG. 12. Once the proximal-most anchoring clip 108b has been inserted into the tissue at its desired location, the user advances the catheter 106 beyond the distal end 104a of the catheter 104 thereby releasing the pins 116a and 116b. As the pins 116a and 116b are removed from the catheter 106 (e.g., by the distally directed force applied thereto by the suture 112), the knot 114 is released from the distal end 106a. The suture 112 may then be drawn proximally from the catheter 106 to tighten the knot 114 and the distal end 106a may then be used to push the knot 114 distally along the suture 112 until the suture 112 is at a desired tension sufficient to draw the anchoring clips 108 and the tissue within which they are embedded together to close the opening. Of course, those of skill in the art will understand that any number of alternative mechanisms including, for example, pull wires, etc., may be employed to release the pins 116 when desired by the operator.

Figure 8:
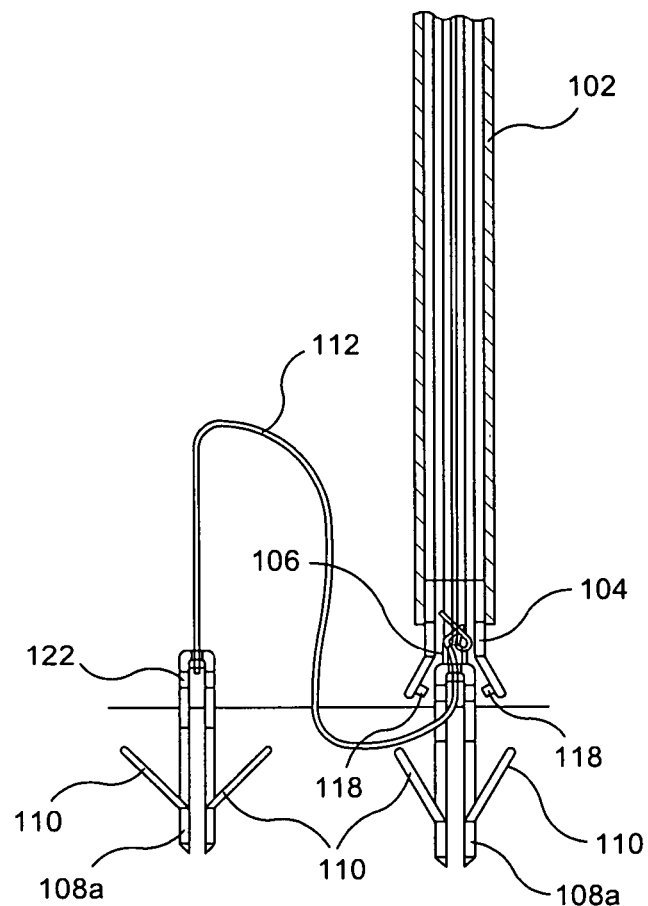
FIG. 8 shows a cross-sectional view of the device of FIG. 7 with first and second anchoring members embedded in tissue before tightening a length of suture extending therebetween.

More specifically, the catheter 104 includes pins 118 formed at the distal end 104a. The pins 118 are mounted on rotatable arms 120 which are biased to rotate away from the axis of the catheter 104. When the catheter 104 is received within the catheter 102, the arms 120 are maintained aligned with the rest of the catheter 104. When in this position, the pins 118 are coupled to the anchoring clip 108b which is currently the distal-most one within the catheter 102. The pins 118 are received within corresponding openings 122 formed near the proximal end of the anchoring clip 118 so that moving the catheter 104 within the catheter 102 moves the distal-most anchoring clip 108 relative thereto. When the distal end 104a advances distally beyond the distal end 102a as shown in FIG. 8, the rotatable arms 120 rotate outward removing the pins 118 from the openings 122 to decouple the anchoring clip 108 from the catheter 104.

In operation, the user passes the catheter 102 including the catheters 104 and 106 received therein, through the working channel of an endoscope to an opening to be sealed and positions the distal end 102a at a desired location for the first anchoring clip 108. The user then withdraws the catheter 104 proximally into the catheter 102 so that the projecting members 110 of the distal-most anchoring clip 108 are released by the catheter 104 and the distal end 102a is placed in contact with the tissue over the desired location. The catheter 106 is then advanced distally through the catheter 104 to advance the tip 109 of the distal-most anchoring clip 108a into the tissue. At this point, the projecting members 110 fully deploy and lock the anchoring clip 108a into the tissue at the desired location. The user then withdraws the catheter 102 proximally relative to the catheter 102 so that the rotatable arms 120 rotate outward removing the pins 118 from the openings 122. The user then withdraws the catheters 102 and 104 proximally away from the anchoring clip 108 and withdraws the catheter 104 proximally into the catheter 102 to bring the arms 120 back into alignment with the rest of the catheter 104 while advancing the catheter 106 distally into the catheter 104 until the pins 118 enter the openings 122 in the next (current distal-most) anchoring clip 108. Thereafter, the user moves the catheter 102 to the desired location for the next anchoring clip 108 and repeats this process until all of the anchoring clips 108 have been embedded in the tissue at the desired locations.

At this point, the suture 112 extends from the distal-most anchoring clip 108a, through each of the succeeding anchoring clips 108 to the proximal-most anchoring clip 108b and from there to the knot 114. The catheter 106 is advanced beyond the distal ends 104a and 102a, releasing the knot 114 from the pins 116a and 116b as the pins 116a and 116b are released as described above. The user then withdraws the suture 112 proximally into the catheter 106 to draw the anchoring clips 108 together and pull the tissue around the opening together to seal the opening. The user then tightens the knot 114 and pushes it against the proximal end of the proximal-most anchoring clip 108b to maintain them in place and uses the suture cutting surface 106a to sever the suture 112. The user then withdraws the catheter 106 into the catheters 102, 104 and withdraws the device 100 from the body.

Figure 14:
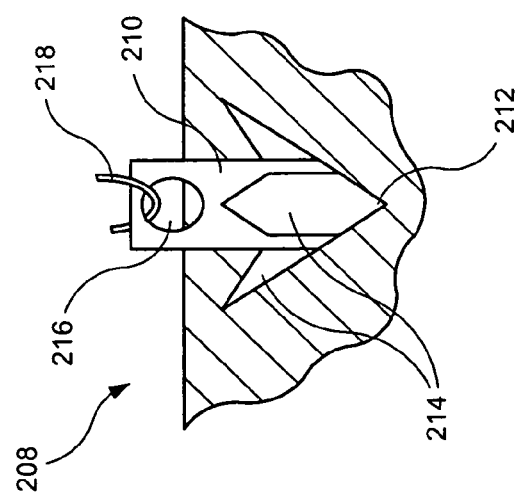
FIG. 14 shows a side view of an anchoring clip according to a first alternate embodiment of the invention.

FIG. 14 shows an anchoring member 208 according to a first alternate embodiment of the invention. The anchoring member 208 includes a shaft 210 extending to a tissue piercing distal tip 212 and projecting members 214 extending outward from the shaft 210. An eyelet 216 is formed at a proximal end of the shaft and a length of suture 218 extends therethrough to couple to the anchoring member 208 to other anchoring members.

Figure 15B:
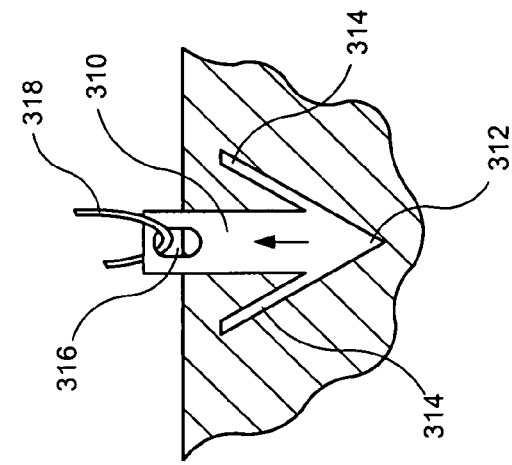
FIG. 15 shows a side view of an anchoring clip according to a second alternate embodiment of the invention in initial and fully deployed positions.
Figure 15A:
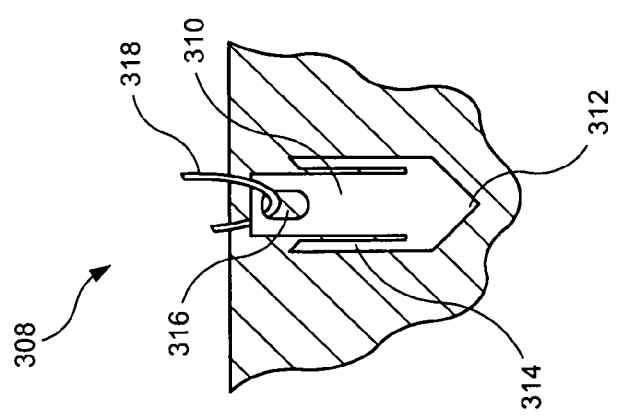

FIG. 15 shows an anchoring member 308 according to a second alternate embodiment of the invention. The anchoring member 308 includes a shaft 310 extending to a tissue piercing distal tip 312 and projecting members 314 coupled to the shaft 310. An eyelet 312 is formed at a proximal end of the shaft and a length of suture 314 extends therethrough to couple to the anchoring member 308 to other anchoring members. The projecting members 314 are initially folded back along the shaft 310 (i.e., during insertion of the anchoring members through the insertion device and during penetration of the tissue). However, once the tip 312 has penetrated the tissue to the extent that proximal ends of the projecting members 314 are embedded in the tissue, drawing the anchoring member 308 toward the surface of the tissue causes the projecting members to spread outward away from the shaft 310, anchoring the anchoring member 308 within the tissue.

FIG. 16 shows an anchoring member 408 according to a third alternate embodiment of the invention. The anchoring member 408 includes first and second tissue gripping ends 412 coupled to a spring member 414 biased to bring the ends 412 toward one another to grasp tissue received therebetween. In FIG. 15, this bias is created by bending the spring member 414 to form a loop 416. A length of suture 418 extends through the loop 416 to couple the anchoring member 408 to other anchoring members.

FIG. 17 shows an anchoring member 508 according to a fourth alternate embodiment of the invention. The anchoring member 508 includes first and second tissue gripping ends 512 coupled to a spring member 514 biased to bring the ends 512 toward one another to grasp tissue received therebetween by bending the spring member 514 to form a loop 516. A length of suture 518 extends through the loop 516 to couple the anchoring member 508 to other anchoring members. In addition, the anchoring member 508 includes abutting members 520 which contact one another when the ends 512 have reached a minimum clearance with respect to one another. This minimum clearance maintained by the abutting members 520 prevents the ends 512 from coming together and severing the gripped tissue.

The above described embodiments are for purposes of illustration only and the various modifications of these embodiments which will be apparent are considered to be within the scope of the teachings of this invention which is to be limited only by the claims appended hereto.

What is claimed is:

1. A device for suturing an opening in an internal organ of a patient, comprising:
   a first catheter for insertion to an opening to be sealed through a working channel of an endoscope, a distal portion of the first catheter including a first hinge formed a predetermined distance from a distal end thereof and a second hinge formed proximally of the first hinge so that, when the distal end of the first catheter contacts a tissue, the distal portion of the first catheter folds into a radially expanded configuration;
   a plurality of anchoring members received within the first catheter, each of the anchoring members including a shaft extending from a tissue penetrating distal tip to a suture receiving proximal end and a gripping arm moveable between an insertion configuration in which the gripping arm is folded against the shaft and a gripping configuration in which the gripping arm extends away from the shaft;
   a first one of the anchoring members including a contact pressure mechanism which releases the gripping arm of the first anchoring member from the insertion configuration when the distal tip of the first anchoring member penetrates the tissue;
   a driving member extending through the first catheter to a proximal end thereof, wherein advancing the driving member distally into the first catheter advances the anchoring members distally through the first catheter to drive a distal-most one of the anchoring members out of the first catheter to anchor in the tissue; and
   a length of suture extending between the suture receiving proximal ends of the anchoring members.

2. The device according to claim 1, wherein the distal portion of the first catheter includes a third hinge formed distally of the first hinge so that, when the distal portion of the first catheter is folded into the radially expanded configuration, the distal end of the first catheter abuts the gripping arm of the distal-most one of the anchoring members to retain a gripping arm of this distal-most catheter in an insertion configuration until a proximal end of the gripping arm passes distally beyond the distal end of the first catheter.

3. A device for suturing an opening in an internal organ of a patient, comprising:
   a first catheter for insertion to an opening to be sealed through a working channel of an endoscope;
   a second catheter slidably received within the first catheter;
   a plurality of anchoring members received within the second catheter, each of the anchoring members including a shaft extending from a tissue penetrating distal tip to a suture receiving proximal end and a gripping arm moveable between an insertion configuration in which the gripping arm is folded against the shaft and a gripping configuration in which the gripping arm extends away from the shaft;
   a driving member slidably received within the second catheter, extending through the second catheter to a proximal end thereof, wherein advancing the driving member distally into the second catheter advances the anchoring members distally through the second catheter to drive a distal-most one of the anchoring members out of the second catheter to anchor in a tissue; and
   a length of suture extending between the suture receiving proximal ends of the anchoring members.

4. The device according to claim 3, wherein the second catheter selectively couples to the distal-most one of the anchoring members so that, after the distal-most one of the anchoring members has been embedded in tissue, the user may release the distal-most one of the anchoring members from the second catheter.

5. A device for suturing an opening in an internal organ of a patient, comprising:
   a first catheter for insertion to an opening to be sealed through a working channel of an endoscope;
   a plurality of anchoring members received within the first catheter, each of the anchoring members including a shaft extending from a tissue penetrating distal tip to a suture receiving proximal end and a gripping arm moveable between an insertion configuration in which the gripping arm is folded against the shaft and a gripping configuration in which the gripping arm extends away from the shaft;

a length of suture extending between the suture receiving proximal ends of the anchoring members; and a driving member extending through the first catheter to a proximal end thereof, wherein advancing the driving member distally into the first catheter advances the anchoring members distally through the first catheter to drive a distal-most one of the anchoring members out of the first catheter to anchor in a tissue;

wherein the driving member includes a knot holding section, a suture cutting surface and a lumen extending therethrough and wherein the suture extends through the lumen to a proximal end of the device.

6. The device according to claim 5, wherein the knot holding section includes a suture holding pin which, in a suture holding configuration, protrudes from the driving member and, in a suture release configuration, is withdrawn into the driving member.

7. A system for suturing an opening within a body, comprising:

an endoscope including a working channel extending therethrough;

a first catheter slidably received within the working channel;

a second catheter slidably received within the first catheter and including a plurality of anchoring members slidably received therein, wherein the anchoring members include projecting members for maintaining the anchoring members in desired positions in tissue, the projecting members being in a retracted state while received within the second catheter;

a third catheter slidably received within the second catheter and extending from a proximal end of the endoscope to a proximal end of a proximal-most one of the anchoring members; and a length of suture extending between the anchoring members.

8. The system according to claim 7, wherein the first catheter includes a contact pressure mechanism which retains the projecting members in the retracted state until they are deployed in tissue.

9. The system according to claim 8, wherein the contact pressure mechanism includes a folding portion of the first catheter which, when pushed against tissue, collapses axially into a radially expanded configuration with a holding surface abutting at least one projecting member of a distal-most one of the anchoring members to maintain the projecting member in the retracted state while in contact therewith.

10. A device for suturing tissue within a body of a patient, comprising:

a first catheter for insertion through a working channel of an endoscope;

a plurality of anchoring members received within the first catheter, each of the anchoring members including a shaft extending from a tissue penetrating distal tip to a suture receiving proximal end and a gripping arm moveably coupled thereto, wherein an extending means of at least a first one of the anchoring members includes a biasing member biasing the gripping arm toward a gripping configuration and wherein the gripping member of the at least the first one of the anchoring members is restrained in an insertion configuration while received within the first catheter by contact between an inner wall of the first catheter and the gripping arm;

a driving member extending through the first catheter to a proximal end thereof, wherein advancing the driving member distally into the first catheter advances the anchoring members distally through the first catheter to drive a distal-most one of the anchoring members out of the first catheter to anchor in tissue, a first one of the anchoring members including extending means for deploying the gripping arm of the first anchoring member from the insertion configuration in which the gripping arm is folded against the shaft to the gripping configuration in which the gripping arm extends away from the shaft when the first anchoring member is deployed from the first catheter into the tissue; and a length of suture extending between the suture receiving proximal ends of the anchoring members.

11. The device according to claim 10, wherein a distal portion of the first catheter includes a first hinge formed a predetermined distance from a distal end thereof and a second hinge formed proximally of the first hinge so that, when the distal end of the first catheter contacts the tissue, the distal portion of the first catheter folds into a radially expanded configuration.

* * * * *